United States Patent [19]
Arnold et al.

[11] Patent Number: 5,310,648
[45] Date of Patent: May 10, 1994

[54] COMPOSITION OF MATTER COMPRISING AN IMPRINTED MATRIX EXHIBITING SELECTIVE BINDING INTERACTIONS THROUGH CHELATED METALS

[75] Inventors: Frances H. Arnold; Pradeep Dhal, both of Pasadena; Deborah Shnek, Pomona; Sean Plunkett, Pasadena, all of Calif.

[73] Assignee: California Institute of Technology, Pasadena, Calif.

[21] Appl. No.: 649,470

[22] Filed: Feb. 1, 1991

[51] Int. Cl.$^5$ .................. A01N 1/02; C12Q 1/70; C12Q 1/04; C12N 5/00
[52] U.S. Cl. ............................ 435/5; 435/2; 435/4; 435/34; 435/7.21; 435/7.23; 435/240.2; 435/235.1; 530/350; 530/395
[58] Field of Search ................. 435/2, 4, 5, 34, 7.21, 435/7.23, 240.2, 235; 530/350, 395

[56] References Cited
PUBLICATIONS

Dodrer, N. and Regen, S., "Polymerized Liposomes Designed to Probe and Exploit Ligand-Receptor Recognition at the Supramolecular Level", J. Am. Chem. Soc. 112 2829-2830 (1990).
Day, D. et al., "Polymerization of Mono- and Bi-functional Diacetylene Derivatives in Monolayers at the Gas-Water Interface", Israel Journal of Chemistry: 18 325-329 (1979).
Fuhrhop, J. and Mathieu, J., "Routes to Functional Vesicle Membranes without Proteins", Angew. Chem. Int. Ed. Engl.:23 100-112 (1984).
Porath, Jerker et al., "Metal chelate affinity chromatography, a new approach to protein fractionation", Nature 258:598-599 (1975).
Gunter Wulff, "Molecular Recognition in Polymers Prepared by Imprinting with Templates", ACS Symp. Ser. 308, 186-230 (1986).
Ekberg, B. and Mosbach, K., "Molecular imprinting: a technique for producing specific separation materials", Tibtech 7:92-96 (1989).

*Primary Examiner*—Robert J. Hill, Jr.
*Assistant Examiner*—Gian P. Wang
*Attorney, Agent, or Firm*—Poms, Smith, Lande & Rose

[57] ABSTRACT

The invention provides an imprinted matrix which exhibits selective binding interactions through metal chelates with a predetermined molecule or biological particle. Also provided is a preformed, fluid-imprinted matrix having sufficient rigidity to maintain selective binding interaction with a predetermined molecule or biological particle through interactive moieties. Methods for producing such matrices are additionally provided.

9 Claims, 3 Drawing Sheets

COMPOSITION OF MATTER COMPRISING AN IMPRINTED MATRIX EXHIBITING SELECTIVE BINDING INTERACTIONS THROUGH CHELATED METALS

BACKGROUND OF THE INVENTION

This invention relates to affinity ligands in general and, more particularly, to methods of producing highly selective matrices with reversible binding characteristics.

Separation and purification accounts for a very large percentage of the production cost of proteins and many specialty chemicals used for human therapeutics. Considerable effort is being expended on developing and optimizing techniques for the large-scale separation and purification of proteins. The difficulties lie in the high degrees of purity required for human therapeutics and therefore the extreme selectivity that is required for the separation process. These requirements result in complex, multi-step processes with concomitant high cost and low yield. Similar considerations hold true for specialty chemicals.

High selectivity in purification appears to be incompatible with low cost. For example, precipitation processes, or even ion-exchange chromatography, are relatively inexpensive operations, but they are also relatively nonselective and often must be accompanied by additional purification steps. Affinity separations often give a very high degree of purification in a single step, but biologically derived ligands such as monoclonal antibodies which are used in affinity chromatography are very costly, are unstable, and are not particularly easy to recycle or sterilize.

Affinity separations have been developed which exploit the affinity exhibited by proteins for metal ions. This property has been utilized in immobilized metal-affinity chromatography (IMAC) of proteins from natural sources and from recombinant organisms. A related technique, known as ligand-exchange chromatography, has been used in the purification of specialty chemicals such as amino acid derivatives and chiral precursors. In these techniques, a chelated metal ion with at least one available coordination site is covalently attached to a solid support and used as an affinity ligand to retain molecules which exhibit metal-coordinating moieties on their surfaces. Examples of such metal coordinating moieties are the amino acid side chains of histidine and cysteine on the surfaces of proteins. IMAC holds a number of important advantages over the use of biologically derived affinity ligands as recognition agents in protein separations. The small metal chelates generally used in metal-affinity separations are stable under a wide range of solvent conditions and temperatures. As a result, they can be recycled numerous times with negligible loss in performance. Other advantages of metal-affinity separations include the high metal loadings and therefore high protein capacities that can be attained and the relative ease of product elution and ligand regeneration. Proteins bound to chelated metals are easily removed by lowering the pH or by introducing a metal-binding ligand such as imidazole, and metal-affinity columns are regenerated simply by replenishing the supply of chelated metal. Metal chelate ligands have the additional advantage of being inexpensive.

Although metal-affinity separations are attractive from a number of economic and practical viewpoints, the metal-affinity ligands used are, unfortunately, not nearly as selective as biologically derived molecules such as antibodies. For example, chromatography on iminodiacetic acid-bound Cu(II), the most commonly used metal chelate, distinguishes proteins primarily by their surface histidine contents. While such current metal-affinity separations distinguish among proteins that contain widely different numbers of exposed histidines, it becomes more difficult to separate those with similar numbers of histidines.

One method to create polymeric matrices which exhibit selective binding interactions is to prepare polymers by a technique known as molecular imprinting or template polymerization. The technique is reviewed in Ekberg and Mosbach, TIBTECH 7:92–96 (1989), and in Wulff, Am. Chem. Soc. Symp. Ser. 308:186–230 (1986), and which describe molecular imprinting of small organic molecules and amino acids. Imprinting utilizes a template molecule with which to orchestrate the synthesis of individual monomers into a polymer matrix. The resulting matrix exhibits a large number of complementary interactions between the monomers and template molecule and can be viewed as a molecular "mold-like" structure. Such polymers are capable of specific recognition of template molecules and have been exclusively limited to small molecules.

A major disadvantage of this molecular imprinting technique is that the chemistry involved in synthesizing such polymer matrices is largely limited to organic solvents. While organic solvents can be used with small organic molecules and amino acids, they cannot be used with biological macromolecules or particles since they result in denaturation and inactivation of such molecules. Another disadvantage is that a large number of interactions are needed to selectively recognize a molecule as large as a protein. It is extremely difficult to synthesize materials with such a large number of complementary interactions.

There thus exists a need for inexpensive compositions which exhibit the high selectivity of biologically derived affinity ligands toward molecules, including macromolecules and biological particles, and yet retain reversible interactive and stability properties of metal-chelate ligands and imprinted polymers. The present invention satisfies these needs and provides related advantages as well.

SUMMARY OF THE INVENTION

The invention provides an imprinted matrix which exhibits selective binding interactions through metal chelates with a predetermined molecule or biological particle. Also provided is a preformed, fluid imprinted matrix having sufficient rigidity to maintain selective binding interaction with a predetermined molecule or biological particle through interactive moieties. Methods for producing such matrices are additionally provided.

DETAILED DESCRIPTION OF THE INVENTION

Figure 1:
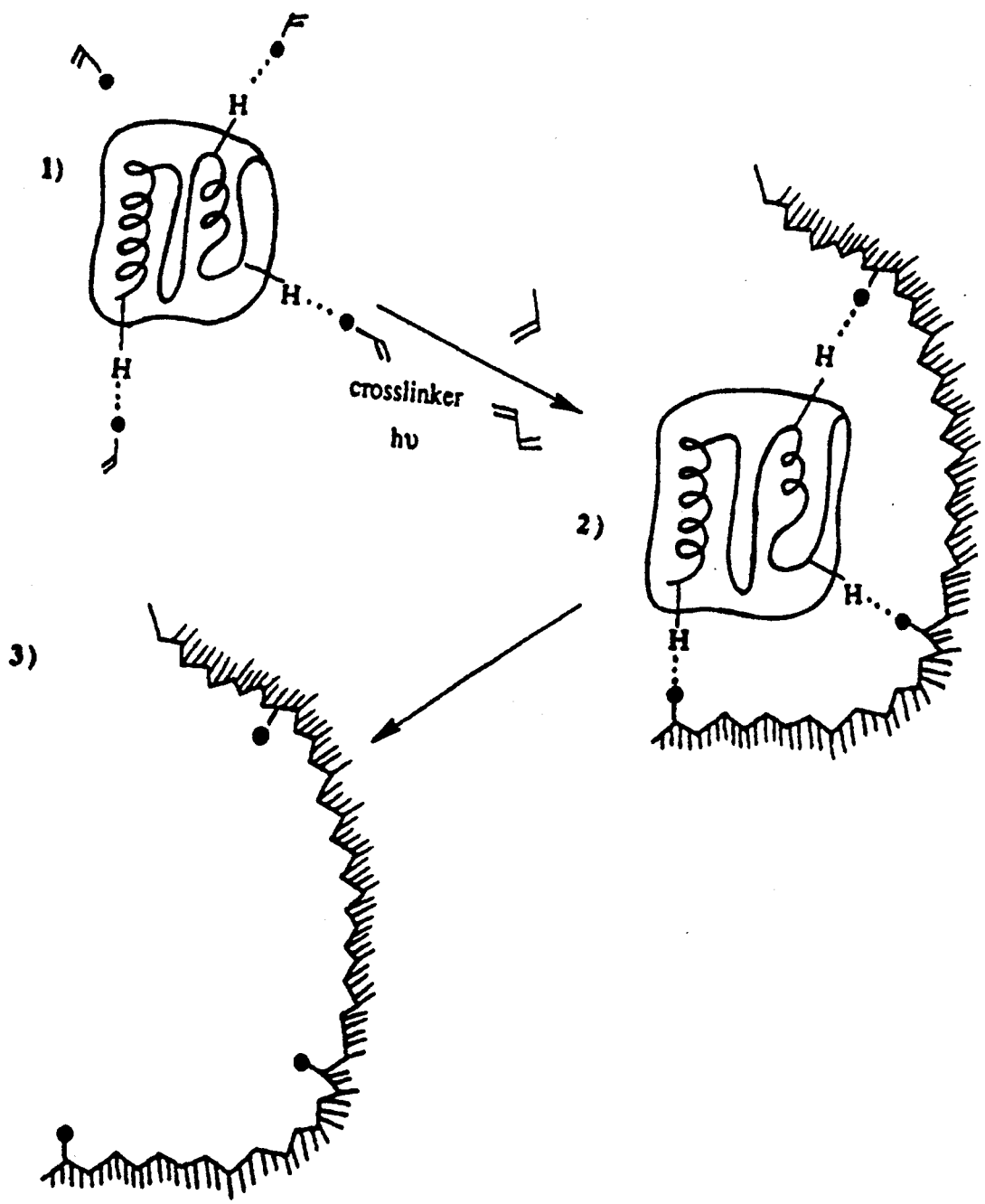
FIG. 1 is a schematic diagram for preparing a molecular imprint of a protein by metal-chelating polymers.

References are cited throughout the specification. These references in their entirety are incorporated by reference into the specification to more fully describe the state of the art to which it pertains.

The invention is directed to a novel class of compositions and methods of making such compositions for imprinting predetermined molecules and biological particles. The compositions are tailored to selectively recognize essentially any desired molecule or aggregate of molecules. Imprinting methods are efficient, inexpensive, and yield matrices which are stable under a variety of conditions. Thus, the imprinted matrices are desirable alternatives to expensive and unstable biologically derived recognition molecules. The imprinted matrices are applicable in a variety of research, therapeutic, diagnostic and manufacturing methods.

In one embodiment, the imprinted matrices are composed of polymers containing chelated metals which bind functional groups on protein surfaces. Chelated metals provide optimal energetic requirements for imprinted matrices since a relatively small number of interactions are needed for selective recognition. The selective recognition is due to the spatial matching of metal ions, for example copper ions, in a rigid polymer to that of metal-coordinating amino acid residues, for example histidines, on the protein surface. Spatial matching is performed by polymerization of the monomers and cross-linking agents in the presence of the protein. Metal-chelating monomers are preorganized prior to polymerization to complement the distribution of coordinating amino acids on the protein surface. Polymerization locks the preorganized monomers into a rigid matrix. Thus, the protein acts as a template to geometrically arrange metal-chelates in the correct three-dimensional structure for selective recognition. The protein template is removed following polymerization, and the resulting imprinted matrix can exhibit selective and reversible affinity for the template protein. Much lower affinities are also observed for proteins whose spatial distribution of coordinating residues does not complement the distance between metal ions.

In another embodiment, ordered fluids such as bilayer membranes are used as imprint matrices instead of solid polymers. Although metals can provide the binding interactions, the preorganized structure of bilayer membranes enables imprinting of large molecules, such as proteins, viruses, or cells without necessitating the use of metal-chelates as affinity ligands. Instead, interactive moieties which bind to functional groups on the template molecule through hydrogen binding, electrostatic interactions, hydrophobic interactions, and van der Waals forces can be used. Metal coordination can also be used. The interactive moieties are attached to the head groups of lipids that are used to form a membrane which is then exposed to the template molecule. The lipids are free to diffuse within the membrane, which allows alignment of interactive moieties with functional groups on the template molecule. Once the geometrical spacing is organized, the lipids are locked in place by chemical cross-linking, forming a two-dimensional imprinted matrix of the template protein. Removal of the template protein yields a membrane with sufficient rigidity to retain spatial organization of interactive moieties for selective and reversible recognition of the template molecule.

As used herein, the term "imprinted matrix" refers to a molecular mold-like structure which has preorganized interactive moieties complementing the spacing of binding sites on a template. The interactive moieties can be, for example, chemical groups or affinity ligands. A specific example of an affinity ligand is iminodiaoetic acid-bound copper(II). The geometrical organization of interactive moieties imparts selective binding characteristics for the template substance onto the imprinted matrix. "Imprinting," as used herein, is the act of spatially organizing the interactive moieties to complement binding sites on a template. Examples of imprinted matrices are, for example, styrene-iminodiacetate metal-chelating monomer cross-linked with ethylene glycol dimethacrylate and stabilized lipid vesicles that contain iminodiacetate-metal head groups and that have been polymerized via diene groups in their lipid tails.

As used herein, the term "selective binding interactions" refers to preferential and reversible binding exhibited by an imprinted matrix for its template molecule compared to other non-template molecules. Selective binding includes both affinity and specificity of the imprinted matrix for its template molecule.

As used herein, the term "preformed fluid imprint matrix" refers to a substance composed of many monomers which are free to diffuse within a two-dimensional space and are organized into a definable structure. A fluid imprint matrix must be able to retain its overall structural integrity when bound to a template molecule. Such monomers of a fluid imprint matrix can be, for example, lipids such as phosphotidylethanolamine and phosphotidylcholine which have been modified in their hydrophilic head groups with interactive moieties Two-dimensional diffusion of the monomers allows complementary spatial organization with the template substance. A specific example of a preformed fluid imprint matrix is a lipid bilayer.

As used herein, the term "predetermined molecule" refers to a substance which has been selected to be used as a template for imprinting. The template molecule can be, for example, small organic molecules such as amino acids, 1,4-naphthyl methyl imidazole and 1,4-benzyl imidazole; larger molecules such as peptides, oligonucleotides, proteins, DNA, and polysaccharides. Such larger molecules are referred to herein as "macromolecules". A template protein is a specific example of a predetermined molecule, (i.e., a protein), which has been selected as a template for imprinting. A "predetermined biological particle," as used herein, refers to template molecules which are composed of aggregates of macromolecules such as cells and viruses.

The invention provides an imprinted matrix exhibiting selective binding interactions through chelated metals with a predetermined molecule or biological particle.

The invention also provides a method of imprinting a predetermined molecule or biological particle. The method consists of: (a) combining a predetermined molecule or biological particle and polymerizable imprint matrix monomers containing chelated metals under conditions where the imprint matrix monomer binds the predetermined molecule or biological particle through interactions with the chelated metals; (b) forming an imprinted matrix from the imprint matrix monomers, the imprint matrix having sufficient rigidity to maintain selective binding interactions between the matrix and the predetermined molecule or biological particle; and (c) removing the predetermined molecule or biological particle from the imprinted matrix.

Small molecules, macromolecules and biological particles are each characterized by an unique spatial distribution of binding sites. Such binding sites can be, for example, nitrogen atoms, amino acid side chains, groups of amino acid side chains, or whole macromolecules. Unique arrangements of binding sites can be used in a general scheme for synthesizing polymers capable of recognizing predetermined molecules or biological particles. For example, specific proteins are each characterized by an unique spatial distribution of surface amino acids. Each surface amino acid constitutes a potential binding site for a variety of different functional groups. Correct spatial arrangement of complementary functional groups and amino acid binding sites allows selective recognition of the protein by the synthesized polymer.

Attempts to orchestrate the synthesis of a large number of weak interactions have yielded matrices which do not exhibit strong binding and high selectivity toward the template molecule. The problem can be attributed to the difficulty of synthesizing compounds that accurately place and retain functional groups in the desired configuration. Additionally, the problem is compounded by the fact that a large number of complementary interactions are needed when each individual interaction, such as hydrogen bonding or van der Waals forces, is relatively weak. As described herein, however, such problems can be overcome for synthesizing imprinted matrix polymers by correct placement of just a few (about 2 to 4) complementary functional groups which exhibit relatively strong and reversible interactions. Functional groups which demonstrate such binding properties are certain chelated metals.

Molecular imprinting utilizes the template molecule to create selective binding sites, thereby obviating the tedious synthesis of prearranged complementary groups. The basic steps for imprinting into a polymer matrix using metal-chelates are shown schematically in FIG. 1 for an imprinting process using protein as template. The binding sites illustrated on the template protein of FIG. 1 are histidines and are denoted as a "H". Free polymerizable monomers containing chelated metals are also shown. Initially, the protein preorganizes the metal ions; that is, it binds to the monomers which contain the chelated metal ions. The chelated metal can be, for example, kinetically labile ions such as $Cu^{2+}$, or they can be inert such as $Pt^{2+}$ or $Ru^{2+}$. Next, the protein-monomer complex is allowed to polymerize in the presence of a cross-linking agent as shown in second step set forth in FIG. 1. The cross-linking agent produces covalent bonds between diene groups on adjacent monomers. Chemical groups other than dienes can also be used. One skilled in the art knows what groups will work and can select the appropriate monomer and cross-linking agent. Polymerization should be sufficient to produce a rigid matrix which maintains the preorganized spatial arrangement of chelated metals. This requirement can be obtained by either polymerization in a large amount of cross-linking agent or, alternatively, adding other monomers which do not contain chelated metals in addition to a moderate amount of cross-linking agent. Metal ions polymerized into the resulting polymer therefore match the spacing of histidines on the protein surface and are immobilized within a solid matrix. Finally the protein is extracted, leaving behind the imprinted polymer matrix as shown in the third step set forth in FIG. 1. The metal used for imprinting can be removed and replaced with another metal if that metal is more suitable for the particular application. Such metals can be, for example, those described above or $Ni^{2+}$, $Zn^{2+}$, $Co^{2+}$, $Cd^{2+}$, or $Ca^{2+}$. The resultant matrix will bind the protein with which it was imprinted with higher affinity than other, similar, though not identical, species.

Metal coordination as the primary reversible interaction in conjunction with proper geometric arrangement of such functional groups allows for high affinity in the presence of about 2 to 4 specific interactions. Only a few interactions are required because the strength of a single interaction is relatively high (3–10 kcal/mol for metal coordination as compared to 1 kcal/mol for hydrogen bonds).

Figure 2A:
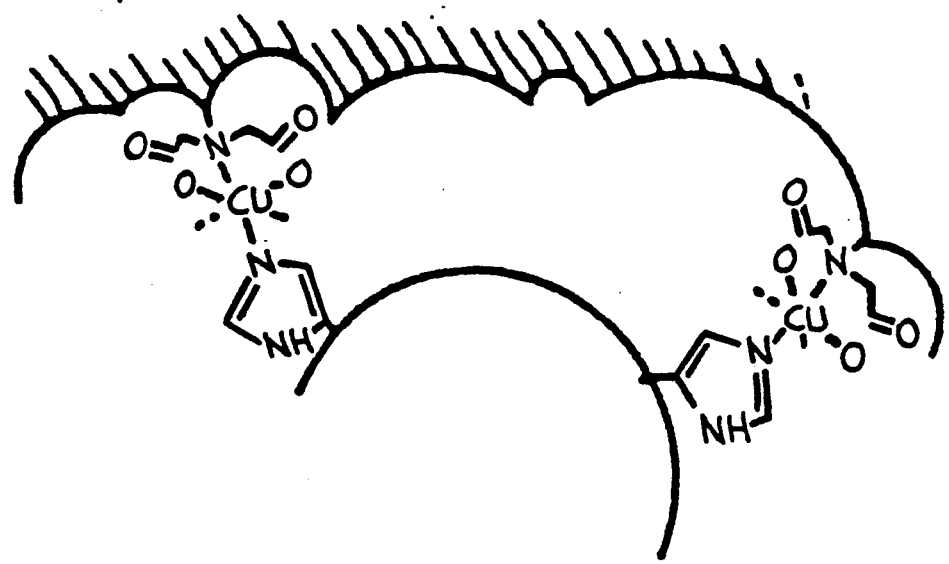
FIG. 2a is a schematic diagram showing binding of the interatcive moieties on the imprinted matrix to a template molecule at two locations.
Figure 2B:
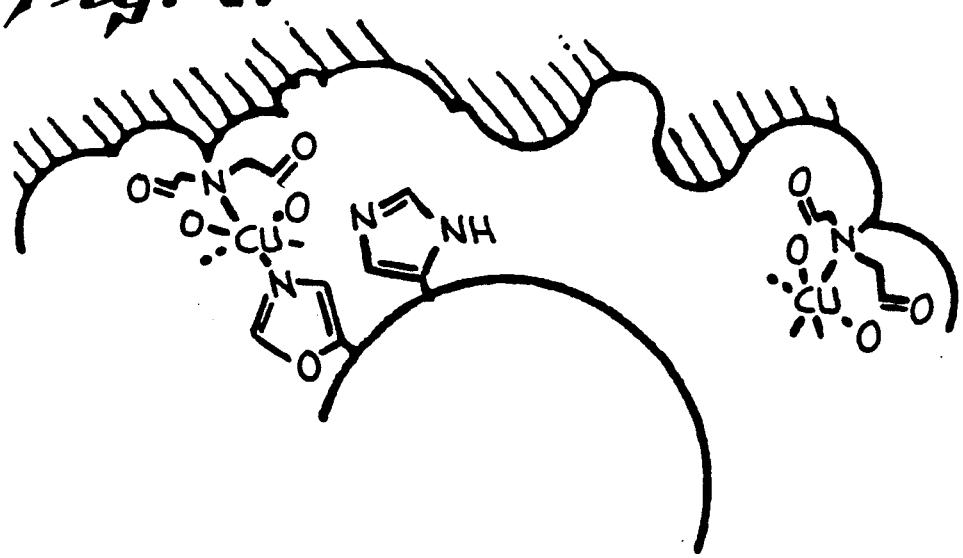
FIG. 2b is a schematic diagram showing binding of the interatcive moieties on the imprinted matrix to a non-template molecule at only one location.

The energetics of metal coordination and its relevance to template recognition is illustrated for a protein in FIGS. 2a and 2b. For example, if the spacing between histidines in a protein is matched by the spacing between metal ions on the imprinted matrix, so that both histidines can bind at once (FIG. 2a), the overall binding constant will be much higher than if only a single histidine can bind (FIG. 2b). Typical values of the association constant for interactions between single histidines and a copper-bound metal chelate such as iminodiacetic acid-bound Cu(II) are $K = 10^{3.6}$ $M^{-1}$ in water. Thus the apparent overall binding constant for the case shown in FIG. 2b is about $2 \times 10^{3.6}$, while that for the case shown in FIG. 2a can be much larger. The magnitude of the binding constant for the case shown in FIG. 2a can be quite large, as high as about $(10^{3.6})^2 = 10^{7.2} M^{-1}$, depending on the flexibility of the protein and the imprinted matrix, strain induced upon binding, and other factors. With three properly positioned metal atoms, binding constants on the order of about $10^9 - 10^{10}$ $M^{-1}$ are conceivable. In contrast, if three hydrogen bonds are used, the maximum stability constant that can be expected is only about $10^4 - 10^5$ $M^{-1}$, five orders of magnitude weaker.

Certain copper chelates are ideally suited for imprinting macromolecules such as proteins. As described above, copper has a high, reversible binding affinity for electron-rich histidines. Histidine is a relatively rare amino acid, comprising about 2% of the amino acids in proteins, of which only about half are surface exposed. Therefore, a protein of about 200 kD will contain an average of about two histidines on its surface. This natural histidine distribution is ideal for imprinting proteins with copper as the chelated metal. However, different molecules, macromolecules and biological particles will have different distributions of functional groups which have affinity for metals other than copper. Ruthenium and nickel are examples of such other metals which can be bound by a chelating agent and used to imprint a substrate. The metal ion used for forming the imprinted matrix must be able to coordinate functional groups on the template molecule. The chelate used to bind the metal must leave at least one metal coordination site available for binding to the template molecule. One skilled in the art knows what functional groups on different print substrates have affinity for which metal-chelates and knows how to substitute the appropriate metal-chelate for a particular print substrate.

The invention provides a preformed fluid imprinted matrix having sufficient rigidity to maintain selective binding interactions through interactive moieties with a predetermined molecule or biological particle.

The invention also provides a method of imprinting a predetermined molecule or biological particle which consists of: (a) combining said predetermined molecule or biological particle and a preformed fluid imprint matrix containing polymerizable monomers and interactive moieties under conditions where the fluid imprint matrix binds the predetermined molecule or biological particle through the interactive moieties; (b) providing sufficient rigidity to the fluid imprint matrix so as to maintain selective interactions between the matrix and the predetermined molecule or biological particle to form an imprinted matrix; and (c) removing the predetermined molecule or biological particle from the imprinted matrix.

Figure 3C:
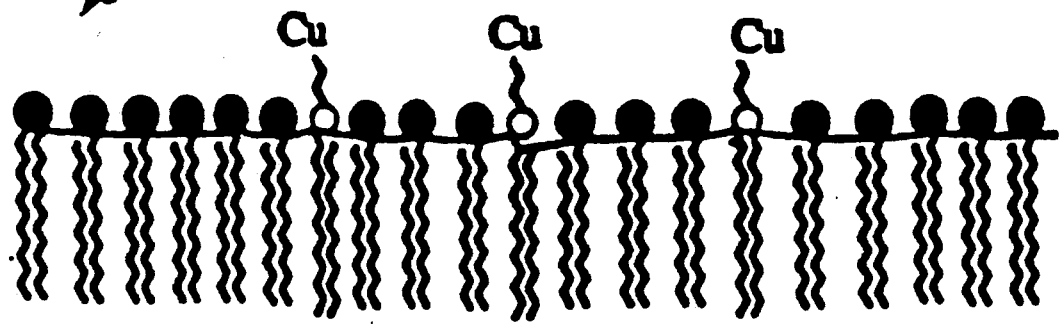
FIG. 3c is a schematic representation showing the imprinted matrix of FIG. 3b after matrix has been polymerized to form a rigid structure and the template for molecule has been removed.
Figure 3A:
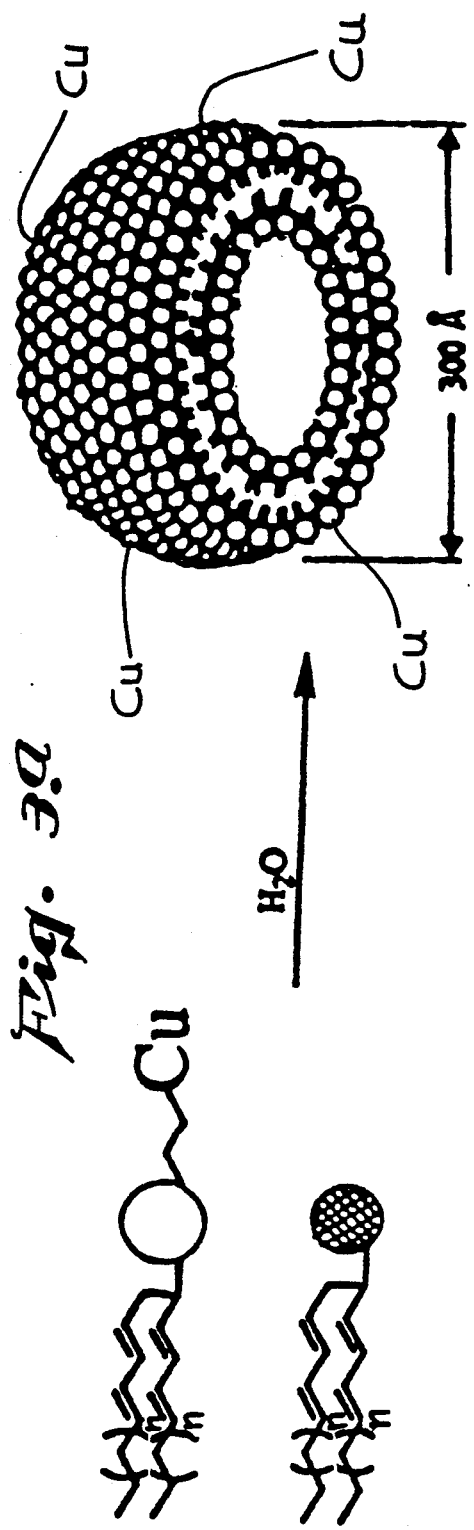
FIG. 3a is a schematic representation of chelated copper attached to a lipid monomers assembled into a membrane structure.

Spatial arrangement of complementary functional groups can also be performed in a preformed fluid imprint matrix. A polymerizable lipid monolayer, membrane or vesicle are specific examples of preformed fluid imprint matrices. Polymerizable membranes are formed from amphiphilic lipid monomers that contain a lipid "tail" and a hydrophilic "head group." Some fraction of these polymerizable monomers contain interactive moieties attached to the head group. These monomers are free to diffuse laterally within the membrane prior to polymerization. Such diffusion of the interactive monomers within an overall stable membrane structure allows imprinted matrices to be made without the use of chelated metals for specific interactions. Such interactions can be hydrogen bonds, hydrophobic interactions, van der Waals forces, and electrostatic interactions between an interactive moiety on the membrane surface and binding sites on the print substrate. Therefore, "interactive moiety" as used herein, refers to a chemical group capable of binding a template molecule through hydrogen bonds, hydrophobic interactions, van der Waals forces, electrostatic interactions or through metal coordination. The interactive moieties can be the head groups of the lipids or moieties specifically attached to the head groups which will have affinity for binding sites on a print substrate. Functional groups possessing positive or negative charges are examples of such attached moieties. Additionally, chelated metals can be employed as the interactive moiety. FIG. 3a shows chelated copper attached to lipid monomers which are assembled into a membrane structure.

The interactive moiety can also be placed on compounds which are soluble in lipid membranes. The compounds can then be added to lipid membranes to incorporate the moieties into the membrane. Porphyrin is an example of such a compound. Porphyrin can embed itself into lipid membranes and once embedded it is free to diffuse laterally within the membrane. As with the monomers previously described, such compounds can be separately prepared and stored. Different derivatized monomers can then be selected for different applications.

Figure 3B:
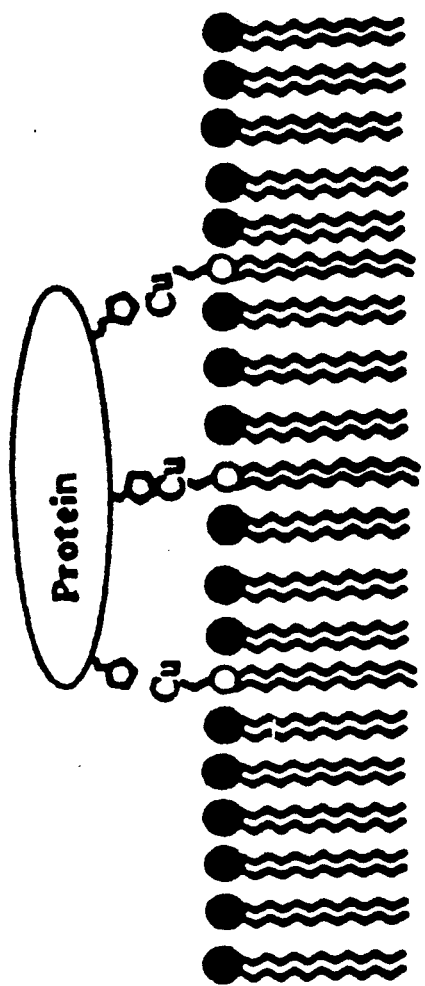
FIG. 3b is a schematic representation showing the spatial arrangement of chelated copper in complementary location with respect to a template molecule.

The interactive moieties arrange themselves by lateral diffusion to complement the print substrate's binding sites (FIG. 3b). The spatial organization can be locked into place to form a rigid structure incapable of lateral diffusion by a variety of means. For example, fluidity can be decreased by polymerization of vinyl, methacrylate, diacetylene, diene, isocyano, and styrene substituents in either the hydrocarbon chains or polar head groups of the lipid monomers. Diene groups on the lipid tails can be polymerized to form rigid structures using radical initiators, UV radiation or qamma radiation (FIG. 3c).

The resulting fluid imprinted matrices have a large surface area accessible for protein binding and can be used, for example, in chromatographic separations, in drug delivery, and for biosensors. Because the polymerization occurs in aqueous solution under mild conditions, fluid imprinted matrices are preferentially suited to maintaining the integrity of biological macromolecules such as proteins and viruses.

The invention provides a polymerizable imprint matrix monomer capable of chelating metals. The imprint matrix monomer can have the structure of the monomer shown in Example III. Polymerizable fluid imprint matrix monomers capable of chelating metals are also provided. Such fluid imprint matrix monomers can be, for example, the monomer of Example IX or X.

It is understood that using any of the imprinting methods described above, the order of attachment of metal chelates or interactive moieties to a monomer and template molecule does not matter. For example, monomers can first be covalently derivatized with metal chelates and then combined with the template molecule. Alternatively, the binding between a template molecule and metal chelates can take place first followed by attachment of the chelating agent to an activated monomer. One skilled in the art will know how to perform such reactions regardless of the order to achieve complementary functional groups for imprinting.

The invention provides a method of using an imprinted matrix for separating a predetermined molecule or biological particle from a material containing the predetermined molecule or biological particle. The method includes the steps of: (a) contacting the material with an imprinted matrix having selective binding interactions for the predetermined molecule or biological particle to form an imprinted matrix-bound complex; (b) separating the imprinted matrix-bound complex from the material; and (c) recovering the predetermined molecule or biological particle from the imprinted matrix-bound complex.

Once produced, the imprinted matrices described herein can be used in essentially any procedure involving affinity ligands. The matrices are more stable than biologically produced affinity ligands and advantageously provide easy recovery of the separated molecules due to the reversible nature of their interaction. For example, an imprinted matrix can be used instead of immobilized antibodies in affinity chromatography for isolating a particular molecule. Imprinted matrices can also be used for targeting therapeutics to cells, separation of viruses from a sample and for separation of cells or organelles from a sample. Material containing the molecule or biological particle is passed over the matrix and eluted under mild conditions after unbound material is first washed away.

The invention provides a method of using an imprinted matrix for detecting the presence of a predetermined molecule or biological particle in a material containing said predetermined molecule or biological particle. The method consists of: (a) contacting the material with an imprinted matrix having selective binding interactions for the predetermined molecule or biological particle to form an imprinted matrix-bound complex; and (b) detecting said imprinted matrix-bound complex.

The imprinted matrixes described herein can also be used in diagnostic procedures. The presence of an analyte in a sample can be determined using an imprinted matrix which selectively recognizes the analyte. The sample containing the analyte is treated with the matrix so as to allow selective binding. The imprinted matrix-bound complex can then be detected using methods known to one skilled in the art. For example, any one of a variety of detectable probes can be attached to the matrix either before or after imprinting. Such detectable probes can include, for example, agents whose fluorescence changes upon formation of the imprinted matrix-bound complex. Complexation can also be detected by measuring changes in certain physical properties of the imprint matrix, such as electrical conductivity.

The following examples are intended to illustrate but not limit the invention.

EXAMPLE I

Synthesis of Metal Chelating Monomers

This example shows the synthesis of metal-chelating monomer N-(4-vinyl)-benzyl iminodiacetic acid. The structure is given below:

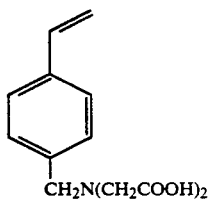

Iminodiacetic acid (8 g; 60 mmol) was dissolved in 120 ml of 50% aqueous methanol containing 4 g (100 mmol) of NaOH and the resulting solution was warmed up to 60° C. While maintained at this temperature, 10.8 g (70 mmol) of 4-vinyl benzylchloride dissolved in 30 ml of methanol was added slowly. After half of the 10.8 g was added, 4 g of NaOH dissolved in 15 ml of methanol was added followed by addition of the remaining benzyl chloride. The reaction mixture was kept at this temperature for 45 minutes. Methanol was distilled off under vacuum to half of its volume. The reaction mixture was allowed to cool and was extracted with diethyl ether (3×100 ml) and the combined organic phase was discarded. The aqueous phase was acidified with 6N HCl to pH 2.5 at which point a white solid mass precipitated. The crude product thus obtained was purified by recrystallization from water (twice) to give a 40% yield.

EXAMPLE II

Synthesis of Copper-Chelating Monomers

This example shows the synthesis of copper-chelating monomer copper(II) N-(4-vinyl)-benzyl iminodiacetic acid.2H$_2$O. The structure of the final product is shown below:

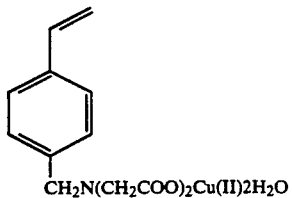

The starting material for synthesis was that produced in Example I. Initially, 5 g (20 mmol) of N-(4-vinyl)benzyl iminodiacetic acid was suspended in 25 ml of water and was neutralized with 1N NaOH to pH 7.0. To this solution, 3.4 g (20 mmol) of Cu(II)Cl$_2$·2H$_2$O dissolved in 15 ml water was added slowly. The resulting deep blue solution was allowed to stir for 5 hours. Subsequently the solvent was removed under vacuum. The residue was treated with 40 ml methanol and filtered off to remove the insoluble inorganic salts. The filtrate was concentrated to half of its volume and left in the refrigerator to give bright blue crystals at a 65% final yield.

EXAMPLE III

Synthesis of Water-Soluble Metal-Chelating Monomers

This example shows the synthesis of novel water-soluble metal-chelating monomer N-[2-dicarboxymethyl)-aminoethyl methacrylamide]. The structure of the final product is shown below:

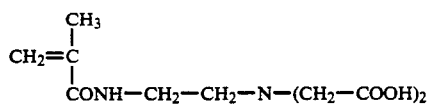

Starting with 1,2-ethylene diamine, this compound was synthesized in four steps as described below:

(i) N-tBoc 1,2-Ethylene Diamine

To 6 g (100 mmol) 1,2--ethylene diamine dissolved in 25 ml of dioxane, 4.4 g (20 mmol) of di-tert-butyl dicarbonate in 40 ml of dioxane was added very slowly with stirring over a period of 4 hours. The reaction mixture was allowed to stir for 24 hours and the solvent was removed under vacuum. To the residue 40 ml of water was added and stirred for ½ hour. The insoluble N,N'-bis t-Boc diamine was removed by filtration. The aqueous solution was extracted with dichloromethane (4×40 ml) and the combined organic phase was dried over Na$_2$SO$_4$. The solvent was evaporated under vacuum to give an oily residue which was recrystallized from isopropanol giving a white solid. The yield was 60%.

(ii) N-(2-amino)-ethyl Methacrylamide HCl 3.2 g (20 mmol) N-tBoc ethylene diamine and 2.53 g (25 mmol) were dissolved in 30 ml chloroform. This reaction mixture was cooled in an ice bath and to it 2.5 g (24 mmol) methacryloyl chloride dissolved in 10 ml chloroform was added slowly. After complete addition the reaction mixture was allowed to warm up to room temperature and stirred for 4 additional hours. The chloroform solution was successively washed with 5% aq Na$_2$CO$_3$, water and brine and dried over Na$_2$SO$_4$. The chloroform was removed under vacuum and the product was recrystallized from ether:hexane. The yield was 72%.

(iii) Conversion of N-(2-amino)-ethyl Methacrylamide.HCl to an Amine

The above t-Boc protected methacrylamimide was converted to the amine by dissolving 3 g of this compound in 20 ml ethyl acetate and to it 5 ml of 6N HCl was added with rapid stirring. The reaction mixture was stirred for 2 hours and then the solvent was removed under vacuum. The oily residue was washed with ether which crystallized upon standing giving a hygroscopic solid. The yield was 90%.

(iv) Synthesis of 3

1.65 g (10 mmol) of the above amino methacrylamide was dissolved in 15 ml of water and was neutralized with 1M NaOH to pH 8.0. 3.5 g (25 mmol) of bromoacetic acid dissolved in 10 ml of water was added slowly to the acrylamide solution. The temperature of the reaction mixture was kept below 4° C. and the pH of the medium was maintained around 9–10 with the intermittent addition of 1M NaOH. After completion of addition, the reaction mixture was allowed to warm up to room temperature and stirred for 24 hours. The reaction mixture was subsequently acidified with 2N HCl to pH 5 and was extracted with ethyl acetate (3×40 ml) to remove unreacted bromoacetic acid. The volume of the water was reduced to half under vacuum and was acidified to pH approximately 2.5. The white precipitate thus obtained was recrystallized from water. The yield was 60%.

EXAMPLE IV

Preparation of Water-Soluble Copper(II)-Chelating Monomer

This example shows the preparation of water-soluble metal-chelating monomer copper(II) N-[2-dicarboxymethyl)-aminoethyl methacrylamide]. The starting material was that synthesized in Example III.

N-[2-dicarboxymethyl)-aminoethyl methacrylamide] (1.22 g) was suspended in 15 ml water and slowly neutralized with 1N NaOH to pH 7.0. 0.85 g of Cu(II)Cl$_2$·2H$_2$O dissolved in 5 ml water was slowly added to this monomer solution. The resulting blue solution was stirred at room temperature for 4 hours. Subsequently, the water was removed under vacuum and 10 ml methanol was added. The insoluble residue was filtered off and the methanolic solution was maintained at −20° C. to obtain the desired copper salt in the form of blue crystals. The crystals were filtered, dried under vacuum, and stored under argon. The final yield was 60%.

EXAMPLE V

Preparation of Imprinted Polymers: Small Molecule Templates

This example demonstrates the preparation of metal-chelating polymers and the reversible removal and replacement of copper ions in the polymer. Further, the selectivity of the polymer for its specific bisimidazole template is clearly demonstrated.

Selective polymers were synthesized on small template molecules that can be considered as protein analogs in that they contain functional groups that are similar to histidine. Specifically, polymers described in this example are able to distinguish between the below two, very similar bisimidazole compounds (1 and 2). These compounds are so similar that they cannot be separated using high-resolution techniques such as reverse phase HPLC. They also are indistinguishable by ligand-exchange (metal-affinity) chromatography on commercially available Cu(II)IDA supports.

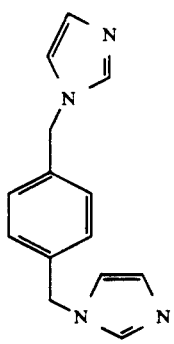

(1)

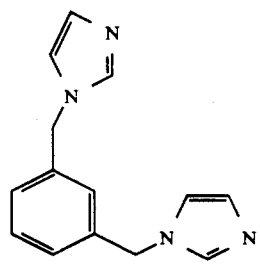

(2)

Synthesis of the metal-chelating monomer used for template polymerization is described in Examples I and II. For preparation of the imprinted polymer, two molar equivalents of copper(II) N-(4-vinyl)-benzyl iminodiacetic acid·2H$_2$O were dissolved in methanol with one equivalent of bisimidazole template (1 or 2) and allowed to equilibrate. The solution color became deeper blue, indicating complexation between the imidazole moieties and vacant Cu(II) coordination sites. Polymerizations were carried out using a 5:95 molar ratio of monomer to crosslinker (ethylene glycol dimethacrylate). After adding the crosslinking agent, the mixture was flushed with argon and polymerization was initiated at 65° C. by free radical initiation with AIBN. The reaction was allowed to proceed for 24 hours at 65° C., after which time the blue, solid polymer was cooled, ground into small particles (150–250 μ), and washed with methanol to remove unbound template and other soluble material.

The bisimidazole templates were removed by washing with 3N HCL (in methanol). Under these conditions, the templates are removed without affecting the metal ion chelated in the polymer. The copper ions were removed by treating the template-free polymers with excess 0.1MEDTA solution. The copper could be reloaded by treating the matrix with excess CuCl$_2$.

The resulting two polymers, P1 and P2, were prepared using 1 and 2 as the template, respectively. The polymerization conditions and the amounts of template and Cu(II) eluted from the polymers are listed in Table I.

TABLE I

| POLYMERIZATION CONDITIONS AND WORKUP OF TEMPLATED POLYMERS | | | | |
|---|---|---|---|---|
| Polymer recovered | [CU(II)] (mmol/g mixture) | [template] (mmol/g) | template recovered (mmol/g) | Cu(II) (mmol/g) |
| P1 | 0.52 | (1) 0.26 | 0.26 | 0.47 |

TABLE I-continued

POLYMERIZATION CONDITIONS AND WORKUP
OF TEMPLATED POLYMERS

| Polymer recovered | [CU(II)] (mmol/g mixture) | [template] (mmol/g) | template recovered (mmol/g) | Cu(II) (mmol/g) |
|---|---|---|---|---|
| P2 | 0.53 | (2) 0.27 | 0.26 | 0.49 |

The binding selectivities for the bisimidazole substrates were evaluated by equilibrating the Cu(II)-loaded polymers with bisimidazole molecules (both template and non-template structures). For these experiments, the polymers were treated with an excess of the substrate for 30 hours at room temperature. Then the polymers were filtered and washed thoroughly with equilibration solvent (methanol:water). The substrate contents of the combined washings were used to determine the uptake by the polymers. The results of binding studies on polymers P1 and P2 are summarized in Table II. Each polymer prefers its template substrate. For example, a gram of P1, synthesized using structure 1 as the template, binds 50% more 1 (0.33 mmol) than 2 (0.22 mmol).

TABLE II

UPTAKE OF BISIMIDAZOLE SUBSTRATES BY
TEMPLATED POLYMERS

| Polymer | substrate contacted with polymer (mmol/g polymer) | substrate bound (mmol/g polymer) |
|---|---|---|
| P1 | 1.31 (1) | 0.33 |
| P1 | 1.52 (2) | 0.22 |
| P2 | 1.45 (2) | 0.24 |
| P2 | 1.6 (1) | 0.17 |

Binding experiments were also carried out using mixtures of compounds 1 and 2 in order to determine the binding selectivities of the templated polymers. In addition, competitive binding was measured to the copper-free polymers. The binding preference for the template structure was also observed in competitive binding experiments when the polymer P1 contains copper (Table III). The separation factor for this (unoptimized) material is 1.17. A separation factor of 1.15 is observed for substrate 2 versus 1 on polymer P2. With the copper removed, the polymers exhibited very little selectivity for a particular substrate compound. Furthermore, the binding capacities of the copper-free polymers were much less than those of the metallated materials (<20%).

TABLE III

COMPETITIVE BINDING OF BISIMIDAZOLE
COMPOUNDS 1 AND 2 TO TEMPLATED POLYMERS
P1 AND P2. POLYMERS ARE CONTACTED WITH
EXCESS BISIMIDAZOLE

| Polymer | mole ratio of 1:2 contacted with polymer | mole ratio of 1:2 bound to polymer |
|---|---|---|
| P1 | 1.0 | 1.17 ($\alpha_{1,2} = 1.17$) |
| P1 (copper free) | 1.0 | 1.04 |
| P2 | 1.0 | 0.87 ($\beta_{2,1} = 1.15$) |
| P2 (copper free) | 1.0 | 0.96 |

These results demonstrate that two very similar metal-coordinating compounds can be separated on the templated polymers and that the chelated metal is critical to the separation. As mentioned previously, compounds 1 and 2 are inseparable using high-resolution techniques such as reverse phase HPLC. In order to determine the individual concentrations in a mixture of the two, it was necessary to resort to proton NMR spectroscopy at high field (300 MHz). The fact that the template polymerized materials that were synthesized, without optimization, can distinguish these two compounds with a respectable separation factor is highly significant.

These results established: 1) the successful preparation of macroporous metal-chelating polymers, 2) the polymers will reversibly bind Cu(II), 3) the Cu(II)-loaded polymers form coordination complexes with imidazole-containing compounds, and 4) these polymers exhibit selectivity for the template with which they were synthesized.

EXAMPLE VI

Metal Replacement Within an Imprinted Matrix

This example demonstrates the replacement of copper by another metal ion, nickel, in the polymer P1 prepared in Example V.

The copper ions of polymer P1 were removed by treating the template-free polymers with excess 0.1 MEDTA solution. The polymer was then reloaded with nickel by treating the material with excess $NiSO_4$, followed by washing with aqueous buffer. The Ni(II) binding capacity of P1 is 0.45 mmol/g polymer.

EXAMPLE VII

Preparation of Imprinted Polymers: Protein Templates

This example demonstrates the preparation of methacrylamide polymer beads with a protein template. It also demonstrates the removal of the copper ion used during polymerization and reloading of the polymer with copper or another metal ion.

One mg copper(II) N-[2-dicarboxymethyl)aminoethyl methacrylamide], prepared as described in Example IV, is initially dissolved in 1 ml MOPS buffer pH 7.5 (prepared from 1 M solution of 3-N (morpholino) propane sulfonic acid and 1M KOH) and is added to 2 ml of a solution of 10 mg of horse heart myoglobin dissolved in the same buffer. The protein-copper-monomer complex is allowed to equilibrate at room temperature with gentle shaking under a nitrogen atmosphere. 3.5 mg of N-methyl methacrylamide comonomer and 40 mg of 1,4 bis(methacryloyl)piperazine crosslinker dissolved in buffer are added to the protein solution, and 0.1 mg ammonium persulfate and 10 μl tetramethylethylenediamine (TEMED) are added to initiate polymerization. The reaction mixture is stirred gently under nitrogen for 48 hours at room temperature to polymerize. After polymerization, the resulting material is lyophilized and ground to achieve appropriate particle sizes. The particles are washed extensively with buffer and 0.1M NaCl to remove nonspecifically-bound template protein and other soluble components.

Removal of template protein and copper bound by metal-affinity interaction to the polymer is achieved by washing the polymer beads with 0.1M EDTA solution. Alternatively, the protein can be removed by treating the polymer with a reducing agent such as cysteine.

For reloading of metal ions, the protein- and copper-free polymer above is treated with an excess of 0.1M $CuSC_4$ (or other copper salt) solution to reload the polymer with copper ion. To load the polymer with a metal ion other than copper, the polymer is treated with an excess of a salt of that metal ion in solution. For example, $NiSO_4$, $ZnCl_2$ are appropriate for loading Ni and Zn metal ions, respectively.

The choice of the comonomer, crosslinker, and the relative ratios of these used for template polymerization dictate many of the physical properties of the resulting polymer, including nonspecific adsorption, porosity, and matrix rigidity. While porosity will influence loading capacity and mass transfer resistances, the microscopic rigidity will strongly influence the capability of these materials to recognize the template protein. If the spatial arrangement of metal ions exactly matches the histidine spacing on the protein, then protein binding is enhanced by increasing rigidity. This phenomenon is a manifestation of the entropic source of the chelate effect; fewer degrees of freedom mean a smaller entropy loss upon binding at the second and later sites. On the other hand, too much rigidity can be detrimental if binding induces small changes in metal or histidine orientation and this causes strain in the system.

EXAMPLE VIII

Preparation of Imprinted Polymers: Protein Templates Using Thin-layer Template Polymerization on Porous Silica The limited accessibility of the specific binding sites in a rigid macroporous polymer can pose difficulties for binding large proteins and for the recovery of functional template protein. For certain applications, polymer beads may not exhibit the macroscopic physical properties that are optimal for large-scale application, such as high mechanical stability or open pore structure. In order to prepare selective binding polymers in conjunction with a well-defined macroporous structure, an alternative procedure is to polymerize in a thin film over the surface of porous beads, or surfaces. This procedure involves the polymerization of the metal-chelating monomer-protein assembly in the presence of macroporous silica beads which bear polymerizable groups on their surfaces. A similar process has been applied to the preparation of silica packings for HPLC separation of textile dyes, Norrlow, O., Glad, M., Mosbach, K., J. Chromatogr. 299:29 (1984), and to prepare packings characterized by very high selectivities for particular dialdehydes, Wulff, G., Heide, B., Helfmeir, G. S., J. Am. Chem. Soc. 108:1089 (1986).

Silica beads possess predetermined pore sizes and mechanical properties, and these can be chosen for optimum large-scale operation. The polymer forms as a thin layer on the pore surfaces whose areas can be very large. The resulting materials are "pellicular" packings and should give maximum accessibility of the binding sites without seriously compromising binding capacity.

Preparation of methacrylate-modified silica were prepared using wide-pore silica particles reacted with a large excess of 3-methacryloxypropyl trimethoxysilane under inert atmosphere in toluene, Norrlow, O., Glad, M., Mosbach, K., J. Chromatogr. 299:29 (1984).

One g methacrylated silica in 10 ml 50 mM sodium phosphate, 0.5M NaCl pH 7.0 was deareated under vacuum for 30 minutes with stirring. A solution of 10 mg horse heart myoglobin in 10 ml of the same buffer was added to the silica, along with 1 mg of copper(II)-N-[2-(dicarboxymethyl)-aminoethyl]methacrylamide. 40 mg of 1,4 bis-methacryloyl)piperazine was added. The mixture was allowed to stand for approximately 1 hour at room temperature. The initiator solution was prepared by combining 10 mg of ammonium peroxydisulfate with 100 µl tetramethylethylenediamine in 10 ml distilled water. This mixture was slowly added over 4 hours to the protein/monomer/silica mixture with gentle stirring. The reaction vessel was left for an additional 48 hours at room temperature.

After the reaction was complete, the supernatant was removed by filtration. The silica beads were washed extensively with 1M NaCl, 0.1 MEDTA. 6.2 mg of the original protein was recovered during the filtration and wash steps.

EXAMPLE IX

Synthesis of Polymerizable Monomers for Fluid Imprinted Matrices

This example demonstrates the synthesis of the polymerizable metal-chelating amphiphilic lipid bis 1,2-(2,4-octadecadienoyl)-sn-glycerol-3-(propyl)iminodiacetic acid (I). This monomer contains an iminodiacetic acid metal-chelating group in the polar, solvent accessible portion of the molecule. The structure of the amphiphile is shown below.

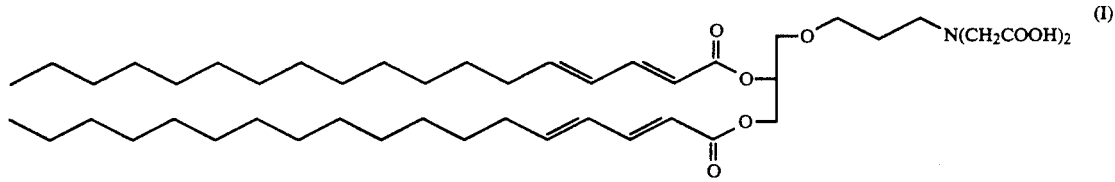

3-aminopropyl solketal was synthesized as described by Misiura et al., Nucleic Acids Res. 18:4345–4354 (1990) with the following modifications. Briefly, 13 g of 2-cyanopropyl solketal in 100 µl of anhydrous ether was added to 3.5 g LiAlH$_4$ in 250 µl of anhydrous ether over 30 minutes, and the mixture was refluxed for 6 hours. After cooling 50 ml of 10% (w/w) aqueous NaOH was added to the mixture, while stirring. The reaction mixture was filtered and the solids refluxed with 100 ml ether for an additional 2 hours. The combined ether phases were evaporated in vacuo, and the residue was distilled under reduced pressure. The pure 3-aminopropyl solketal was dissolved in 40 ml of methanol. A solution of 3.05 g chloroacetic acid in 60 ml of water adjusted to pH 11 was slowly added to the methanol solution. The pH of the reaction medium w$_t$, maintained at pH 11 by intermittent addition of NaOH, and the reaction mixture was stirred for 24 hours at 35° C. The mixture was subsequently extracted with ether and the methanol evaporated. The pH of the resulting solution was brought to 1.8–2.0, at which point the 3-(iminodiacetic acid)ethyl glycerol crystallized.

An alternative procedure to synthesize this compound is by alkylation of the 3-aminoethyl solketal with ethylchloroacetate and Na$_2$CO$_3$ in acetonitrile. Briefly, the mixture was refluxed for 24 hours and the carbonate was removed by filtration. The 3-(diethyl iminodiacetate) solketal was purified by flash chromatography using chloroform:methanol [9:1] as the eluant. The solketal protecting group and the ester were cleaved in dry MeOH/DMF with 6N HCl.

2,4-octadecadienal was synthesized according to Ringsdorf, H., J Macromolec. Sci. Chem. 15:1013-1026 (1981). Briefly, 2,4- octadecadienoic acid was synthesized from 2,4-octadecadienal following the silver dioxide oxidation method of Corey et al., J. Am. Chem. Soc. 90:5616-5617 (1968). The coupling of the acyl chains to the 3-(iminodiacetic acid)propyl glycerol was carried out using dicyclohexyl carbodiimide (DCC)/4-N,N-dimethyl amino pyridine (DMAP) in DMF or CHCl₃, as outlined by Hupfer et al., Chem. Phys. Lipids 33:355-374 (1983).

An alternative approach to synthesizing the above monomer involves treating 2,4-octadecadienoic acid chloride with 3-(iminodiacetic acid)ethyl glycerol by an interfacial condensation approach. The 2,4-octadecadienoic acid chloride was synthesized by oxalyl chloride treatment of the acid following the procedure for unsaturated acids of Serrano et al., Macromolecules 18:1999-2005 (1985).

EXAMPLE X

Synthesis of Metal-chelating Monomers for Polymerizable Fluid Imprinted Matrices This example demonstrates the synthesis of the polymerizable metal-chelating amphiphilic lipid rac-1,2-bis(2,4-octadecadienoyl)-sn-glycerol-3-phosphoryl (ethyl)iminodiacetic acid. The structure is shown below and contains an iminodiacetic acid metal-chelating group in the polar, solvent accessible portion of the molecule as does the monomer of Example IX.

(II)

Briefly, 2,4- octadecadienoyl chloride is synthesized as described in Example IX. The solketal (1,2-isopropylidene-sn-glycerol) is reacted with β,β,β-trichlorethylcarbonate solketal to produce 3-β,β,β-trichloroethylcarbonate solketal, as described by Baer, E., Biochem. Prep. 2:31 (1952). The isopropylidene group is cleaved by HCl hydrolysis to yield (50%) 3-β,β,β-trichloroethylcarbonate-sn-glycerol, Pfieffer, F. R., Miao, C. K. Weisbach, J. A., J. Org. Chem. 35:221-224 (1970). Crude product is reacted directly with 2,4-octadecadienoyl chloride in the presence of triethylamine. Selective hydrolysis using zinc-glacial acetic acid reagent affords the 1,2--bis(2,4-octadecadienoyl)-sn-glycerol, which is purified by recrystallization from petroleum ether.

2-bromoethyl phosphoric dichloride is synthesized from POCl₃ and 2-bromoethanol according to the method of Eibl et al., Chem. Phys. Lipids 22:1-8 (1978). The 1,2-bis(2,4-octadecadienoyl)-sn-glycerol is reacted with 2-bromoethyl phosphoric dichloride in the presence of triethylamine at 0° C. in dichloroethane with stirring. Precipitated triethylammonium hydrochloride is removed by filtration, and the filtrate is evaporated. The subsequent workup is adopted from Hupfer et al., supra. Briefly, the resulting 1,2-bis(2,4-octadecadienoyl)-sn-glycerol-3-phosphoryl bromoethyl ester is reacted directly with iminodiacetic acid at pH 10-11 in methanol:water. Alternatively, this synthesis can be performed by reaction of 1,2-bis(2,4-octadecadienoyl)-sn-glycerol-3-phosphoryl bromoethyl ester with diethyl iminodiacetate in DMF. After coupling, the ester functionality is removed by selective hydrolysis.

The resulting product is purified by Florisil chromatography as described by Hupfer et al., Chem. Phys. Lipids 33:355-374 (1983). Alternatively, silical gel chromatography can be employed using CHCl₃/CH₃OH/NH₃ as eluent.

EXAMPLE XI

Synthesis of Comonomers for Fluid Imprinted Matrices

This example demonstrates the synthesis of the polymerizable lipid rac-1,2-bis(2,4-octadecadienoyl)-sn-glycerol-3-phosphoric acid (III). This polymerizable lipid is shown below and does not contain a metal-chelating group. It serves as a comonomer for liposome formation.

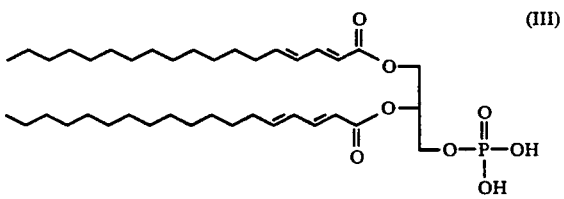

(III)

Briefly, 2,4--octadecadienoyl chloride is synthesized as described in Example IX. rac-α-glyceroliodohydrin is synthesized from solketal (1,2-isopropylidene-sn-glycerol) tosyl chloride and sodium iodide according to Baer and Fischer, J. Am. Chem. Soc. 70:609 (1948). rac-α-glycerol-iodohydrin is reacted with 2,4-octadecadienoyl chloride in the presence of triethylamine in dry DMF. This product can also be made by reacting 2,4-octadecadienoic acid with rac-α-glycerol-iodohydrin using dicyclohexylcarbodiimide (DCC)/4-N,N-dimethylaminopyridine (DMAP) reagent method as described in Example X.

The polymerizable phosphatidic acid lipid is synthesized as described by Rosenthal, Methods Enzymol. 35:429 (1975). Silver di-tert-butyl phosphate is added to bis(2,4--octadecadienoyl) glycerol-3-iodohydrin in anhydrous chloroform. The mixture is reacted at room temperature for one hour and the precipitated silver iodide is removed by centrifugation. Tert-butyl ester groups are removed by gaseous HCl bubbled through chloroform. The lipid is isolated in the form of its barium salt and is purified according to Rosenthal, Supra.

EXAMPLE XII

Preparation of Fluid Imprinted Matrices: Protein Templates

This example describes the preparation of protein-imprinted liposomes by template polymerization. In this process, the ability of amphiphilic molecules to self-assemble into ordered bilayer structures is exploited. A lipid containing an interactive moiety in the solvent-accessible portion of the molecule can diffuse laterally in the bilayer membrane to match the distribution of complementary functional groups on the protein surface.

The liposomes of this example are composed of a small amount of metal-chelating lipid monomer (synthesized in Examples IX or X) and a large amount of lipid comonomers (synthesized in Example XI). Furthermore, all the lipid components of the bilayer are polymerizable in that they contain reactive moieties which allow stabilization of the templated liposome by covalent cross-linking. To "fix" the imprinted spatial distribution of metal ions on the membrane surface, the lipids are polymerized in the presence of the template molecule using UV light and/or a radical initiator. Alternatively, polymerization can be induced using gamma-radiation. When the template protein has been removed, the resulting liposome has a high affinity for that molecule via the particular distribution of metal ions fixed on the liposome surface.

Small amounts of the Cu(II)IDA-lipids of Example IX or Example X are combined with the non-metal-containing comonomer amphiphile of Example XI to prepare small unilamellar vesicles. Standard techniques known to one skilled in the art are used and are described in New, R.R.C., ed., Liposomes: A Practical Approach, Oxford University Press, New York (1990). The optimal relative ratio of metal-chelating monomer to comonomer is dictated by the choice of protein and its surface histidine content, as well as by the desired selectivity and protein-binding capacity. For example, preparation of liposomes that selectively bind myoglobin (4–5 surface histidines), a relative molar ratio of 0.01 I:III is used.

After the liposomes are formed, they are treated with 0.1M CuSC4 solution to load the metal-chelating lipids with Cu(II). The liposomes are extensively washed to remove all unbound Cu(II). Alternatively, the liposome can be formed using the metallated form of monomers which obviates the need for the Cu(II)-loading step.

The vesicles are equilibrated with a solution of the template protein (at neutral pH or above) to allow for the diffusion of the metal-containing amphiphiles to match the surface histidyl distribution of the template protein. The liposome-protein complexes are gradually cooled below the phase transition temperature of the mixed membrane to prevent dissociation of the complex and liposome coalescence. The polymerization is carried out in a well-stirred quartz reaction vessel exposed to a powerful UV source. The extent of polymerization is monitored spectrophotometrically by the disappearance of the dienoyl absorbance at 254 nm.

Subsequent to polymerization, the removal of the template protein and the copper ions from the liposome is accomplished by treating the liposomes with EDTA or other reagents which bind the metal ion, as described in the previous examples.

The references referred to above are hereby incorporated by reference.

Although the invention has been described with reference to the presently-preferred embodiment, it should be understood that various modifications can be made by those skilled in the art without departing from the invention. Accordingly, the invention is limited only by the following claims.

We claim:

1. A composition of matter which selectively binds to one or more functional groups present at spaced locations on the surface of a template molecule, said composition comprising:
   an imprinted matrix comprising a polymer structure which is spatially matched to the surface of said template molecule;
   one or more interactive moieties located on said polymer at spaced locations which are complementary to said functional groups of said template molecule, said interactive moieties comprising chelated metals wherein said chelated metals are located so as to undergo selective binding interactions with said functional groups to thereby provide selective binding of said composition of matter to said template molecule.

2. A composition of matter according to claim 1 wherein said imprinted matrix is spatially matched to the source of a template molecule comprising a macromolecule, said macromolecule including functional groups and wherein said interactive moieties are located at spaced locations on said imprinted matrix which are complementary to the functional groups present on said macromolecule.

3. A composition of matter according to claim 1 wherein said imprinted matrix is spatially matched to the surface of a template molecule comprising a cell or virus, said cell or virus including functional groups and wherein said interactive moieties are located at spaced locations on said imprinted matrix which are complementary to the functional groups present on said macromolecule.

4. A composition of matter according to claim 1 wherein said chelated metals are selected from the group consisting of Pt, Ru, Cu, Fe, Ni, Zn, Co, Cd and Ca.

5. A composition of matter according to claim 1 wherein said polymer structure is made from N-(4-vinyl)-benzyl iminodiacetic acid monomers.

6. A composition of matter according to claim 1 wherein said imprinted matrix is a lipid membrane.

7. A composition of matter according to claim 6 wherein said lipid membrane comprises the polymerizable monomer (bis 1,2-(2,4-octadecadienoyl)-sn-glycerol-3-(propyl) iminodiacetic acid.

8. A composition of matter according to claim 6 wherein said lipid membrane comprises the polymerizable monomer rac 1,2-(2,4-octadecadienoyl)-sn-glycerol-3-phosphoryl(propyl) iminodiacetic acid.

9. A composition of matter according to claim 6 wherein said lipid membrane comprises the polymerizable monomer rac 1,2-bis (2,4-octadecadienoyl)-sn-glycerol-3-phosphoric acid.

* * * * *